US011432961B2

United States Patent
Heeren et al.

(10) Patent No.: US 11,432,961 B2
(45) Date of Patent: Sep. 6, 2022

(54) AUTOMATED VISCOUS FLUID CONTROL IN VITREORETINAL SURGERY

(71) Applicant: Novartis AG, Basel (CH)

(72) Inventors: Tammo Heeren, Aliso Viejo, CA (US); Andrew David Johnson, Laguna Niguel, CA (US)

(73) Assignee: Alcon, Inc., Fribourg (CH)

( * ) Notice: Subject to any disclaimer, the term of this patent is extended or adjusted under 35 U.S.C. 154(b) by 844 days.

(21) Appl. No.: 15/591,498

(22) Filed: May 10, 2017

(65) Prior Publication Data
US 2017/0333253 A1    Nov. 23, 2017

Related U.S. Application Data

(60) Provisional application No. 62/337,681, filed on May 17, 2016.

(51) Int. Cl.
*A61F 9/00* (2006.01)
*A61F 9/007* (2006.01)
(Continued)

(52) U.S. Cl.
CPC ............ *A61F 9/00781* (2013.01); *A61B 3/16* (2013.01); *A61F 9/0017* (2013.01);
(Continued)

(58) Field of Classification Search
CPC .............. A61F 9/00781; A61F 9/00736; A61F 9/0008; A61F 9/0017; A61B 3/16;
(Continued)

(56) References Cited

U.S. PATENT DOCUMENTS 4,722,350 A    2/1988  Armeniades
5,200,430 A *  4/1993  Federman ............ A61K 9/0048
424/9.1
(Continued)

FOREIGN PATENT DOCUMENTS

CN    102711593 A    10/2012
CN    103889374 A     6/2014
(Continued)

OTHER PUBLICATIONS

Kashani, et al., "Methods and Systems for Delivering Material to a Body Part," U.S. Appl. No. 16/505,227, filed Jul. 8, 2019, 23 pages.

*Primary Examiner* — Nathan R Price
*Assistant Examiner* — Courtney B Fredrickson

(57) ABSTRACT

Ophthalmic surgical devices, systems, and methods for automatically controlling the injection or extraction of viscous fluids from a patient's eye are provided. A syringe pump connected with an actuation line and a powered syringe provides pressures for viscous fluid injection or extraction in a vitreous chamber of the eye. A sensor disposed adjacent to or inside the eye determines sensor data relating to an intraocular pressure (IOP). The controller receives the sensor data and regulates the injection or extraction of the viscous fluid in response to the detected IOP, such as by controlling the syringe pump. The controller may determine whether the IOP is above an upper threshold or below a lower threshold and may control the syringe pump to regulate the injection or extraction of viscous fluid to maintain the IOP between the upper and the lower thresholds.

14 Claims, 5 Drawing Sheets

(51) Int. Cl.
*A61M 5/142* (2006.01)
*A61M 5/168* (2006.01)
*A61B 3/16* (2006.01)
*A61M 5/172* (2006.01)

(52) U.S. Cl.
CPC ......... *A61F 9/00736* (2013.01); *A61M 5/142* (2013.01); *A61M 5/16877* (2013.01); *A61M 5/1723* (2013.01); *A61M 2005/14208* (2013.01); *A61M 2005/1726* (2013.01); *A61M 2205/3344* (2013.01); *A61M 2205/502* (2013.01); *A61M 2205/52* (2013.01); *A61M 2210/0612* (2013.01)

(58) Field of Classification Search
CPC .......... A61M 5/142; A61M 2005/1726; A61M 1/0058; A61M 5/16877; A61M 2205/3344
See application file for complete search history.

(56) References Cited

U.S. PATENT DOCUMENTS

| | | | |
|---|---|---|---|
| 5,865,764 A * | 2/1999 | Moorhead | A61M 3/0258 600/561 |
| 6,290,690 B1 * | 9/2001 | Huculak | A61M 1/0058 604/140 |
| 6,491,661 B1 | 12/2002 | Boukhny | |
| 7,326,183 B2 | 2/2008 | Nazarifar | |
| 7,470,277 B2 | 12/2008 | Finlay | |
| 7,524,299 B2 | 4/2009 | Hopkins | |
| 7,713,237 B2 | 5/2010 | Nazarifar et al. | |
| 8,070,711 B2 * | 12/2011 | Bassinger | A61M 1/0062 604/22 |
| 8,109,937 B2 * | 2/2012 | Huculak | A61M 1/0058 600/561 |
| 8,246,580 B2 | 8/2012 | Hopkins | |
| 8,287,486 B2 | 10/2012 | Injev | |
| 8,430,840 B2 | 4/2013 | Nazarifar et al. | |
| 8,920,335 B2 | 12/2014 | Huculak | |
| 9,022,968 B2 * | 5/2015 | Passaglia | A61F 9/00781 604/8 |
| 9,517,162 B2 | 12/2016 | Huculak | |
| 9,931,447 B2 | 4/2018 | Layser | |
| 10,182,939 B2 * | 1/2019 | Canelli | A61F 9/00736 |
| 2008/0281254 A1 * | 11/2008 | Humayun | A61B 90/98 604/22 |
| 2013/0138035 A1 * | 5/2013 | Huculak | A61F 9/00736 604/28 |
| 2013/0150782 A1 | 6/2013 | Sorensen | |
| 2014/0114236 A1 * | 4/2014 | Gordon | A61M 1/0031 604/28 |
| 2014/0163455 A1 | 6/2014 | Wilson | |
| 2015/0148615 A1 | 5/2015 | Brennan | |
| 2015/0148836 A1 | 5/2015 | Heeren | |
| 2017/0326000 A1 | 11/2017 | Heeren | |
| 2017/0333253 A1 | 11/2017 | Heeren | |
| 2018/0228647 A1 * | 8/2018 | Escaf | A61F 9/0008 |

FOREIGN PATENT DOCUMENTS

| | | |
|---|---|---|
| CN | 105324094 A | 2/2016 |
| WO | WO2002017833 A1 | 3/2002 |
| WO | WO2012092018 A1 | 7/2012 |

* cited by examiner

AUTOMATED VISCOUS FLUID CONTROL IN VITREORETINAL SURGERY

PRIORITY CLAIM

This application claims the benefit of priority of U.S. Provisional Patent Application Ser. No. 62/337,681 titled "Automated Viscous Fluid Control in Vitreoretinal Surgery", filed on May 17, 2016, whose inventors are Tammo Heeren and Andrew David Johnson, which is hereby incorporated by reference in its entirety as though fully and completely set forth herein.

TECHNICAL FIELD

The present disclosure relates to ophthalmic surgical devices, systems, and methods. More particularly, but not by way of limitation, the present disclosure relates to devices, systems, and methods for automating viscous fluid control for the filling and removal of liquid tamponades in a patient's eye during an ophthalmic surgical procedure.

BACKGROUND

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

During vitreoretinal surgery, a viscous fluid, such as a liquid tamponade (e.g., silicone oil or perfluoron) may be used to seal retinal tears and allow for scar formation. The user/surgeon may control the injection of the liquid tamponade via a foot pedal and may provide the pressure required to push the relatively viscous liquid tamponade (e.g., about 5,000 cP silicone oil) through a trocar cannula into the vitreous chamber. If the user/surgeon becomes distracted during the filling process, the liquid tamponade may overfill the vitreous chamber and generate unacceptable high intraocular pressure (IOP) in the vitreous chamber. Similarly, in a liquid tamponade extraction procedure, the high viscosity of the liquid tamponades may render it difficult to extract. This may undesirably lead to sustained or prolonged high intraocular pressure in the eye. Thus, there is a need for improved ophthalmic surgical devices, systems, and methods.

SUMMARY

In some exemplary aspects, the present disclosure is directed to an ophthalmic surgical system that includes viscous fluid control system for automating the injection and extraction of liquid tamponades in a patient's eye during an ophthalmic surgical procedure. The system may include a syringe pump connected to an actuation line. The syringe pump may provide pressures for viscous fluid injection into or extraction from a vitreous chamber of an eye of a patient through the actuation line. The system also may include a controller that receives sensor data relating to an IOP of the eye and controls the syringe pump to regulate the viscous fluid injection or extraction based on a comparison of the IOP to a pressure threshold value.

In some implementations, the controller may also determine whether the IOP is above an upper threshold and control the syringe pump to reduce or stop an injection pressure in response to the IOP being above the upper threshold. The controller further may determine whether the IOP is below a lower threshold and control the syringe pump to reduce or stop an extraction pressure in response to the IOP being below a lower threshold.

Some implementations include a foot pedal system that receives user input for controlling the injection/extraction of the viscous fluid in the eye. The controller may control the syringe pump based on the user input received at the foot pedal system when the IOP is below an upper threshold and above a lower threshold. When the IOP is above the upper threshold or below the lower threshold, the controller may override the user input received from the foot pedal system.

In additional exemplary aspects, the present disclosure is directed to an ophthalmic surgical system that may include an actuation line, an infusion line, a powered syringe, and a console for regulating injection or extraction of viscous fluid in a patient's eye during an ophthalmic surgical procedure. The infusion line may have a proximal end, a distal end, and an infusion passage extending therethrough, and the distal end of the infusion line may be configured to enter into a vitreous chamber of the patient's eye. The actuation line may have a proximal end and a distal end. The powered syringe may be coupled to the distal end of the actuation line. The console may be coupled to the proximal end of the infusion line and the proximal end of the actuation line, and may include a syringe pump, an infusion chamber, an infusion pump, and a controller. The syringe pump may be configured to provide pressures for viscous fluid injection or extraction in the vitreous chamber. The infusion chamber may be in fluid communication with the infusion passage, and the infusion pump may be configured to provide low viscosity fluid infusion from the infusion chamber to the vitreous chamber through the infusion passage. The controller may be configured to receive sensor data relating to an IOP of the patient's eye, and regulate the viscous fluid injection/extraction based on a comparison of the IOP to a pressure threshold value.

In some implementations, the system may further include one or more sensors disposed adjacent to and/or in the patient's eye. The one or more sensors may be configured to detect, at a location adjacent to and/or in the patient's eye, the IOP and generate and provide the sensor data to the controller. For example, the one or more sensors may be disposed adjacent to and/or at the distal end of the infusion line.

In another exemplary aspect, the present disclosure is directed to a method of treating an ophthalmic condition. The method may include receiving sensor data from a sensor adjacent to or in an eye of a patient and monitoring an intraocular pressure (IOP) of the eye based on the sensor data. The method may further include determining whether the IOP is above an upper threshold or below a lower threshold. The method may also include, in response to determining that the IOP is above the upper threshold, stopping or reducing a viscous fluid injection, and in response to determining that the IOP is below the lower threshold, stopping or reducing a viscous fluid extraction.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices, systems, and methods disclosed herein and together with the description, serve to explain the principles of the present disclosure.

Figure 1:
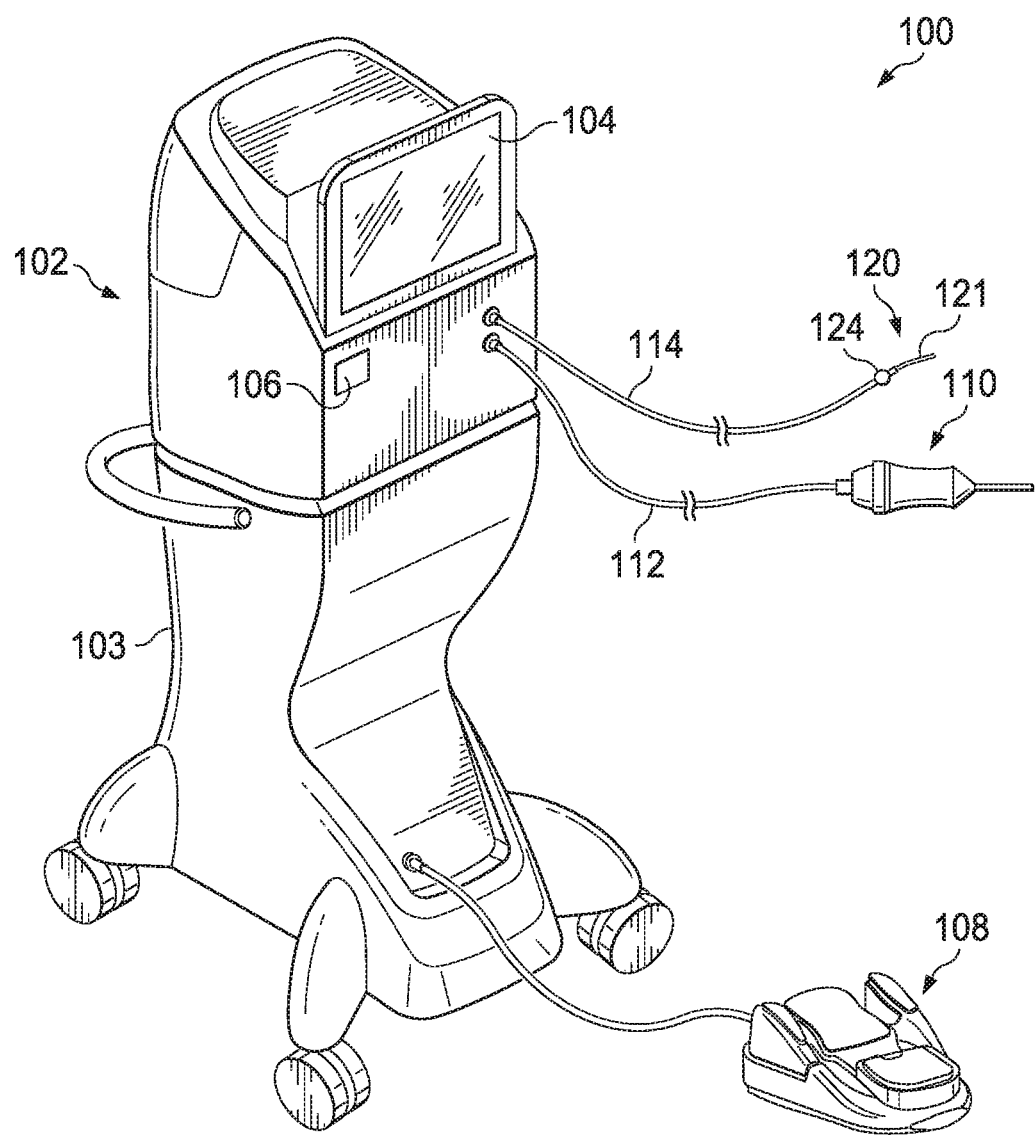
FIG. 1 is an illustration of a surgical system according to exemplary aspects of the present disclosure.

These figures will be better understood by reference to the following Detailed Description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, systems, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to devices, systems, and methods for automating the injection and removal of liquid tamponades in a patient's eye based on an intraocular pressure (IOP) as detected at a location adjacent to or in a patient's eye during ophthalmic surgical procedures. Pressure changes and excessively low or high pressures can complicate the performance of such procedures, putting the patient at risk. In some aspects described herein, an infusion line may include sensors, such as a pressure sensor and/or a flow rate sensor disposed adjacent to or at a distal end, that enter into a vitreous chamber of the patient's eye. The devices, systems, and methods disclosed herein may enable a surgeon to better monitor important pressures and to react quickly to pressure spikes or drops that arise during an ophthalmic surgical procedure. Further, the system may automatically adjust the injection/extraction of the liquid tamponade in response to the detected IOP. By improving the surgeon's abilities or by enabling the system to respond to pressure conditions during an ophthalmic surgical procedure, outcomes for patients may be improved.

Figure 3:
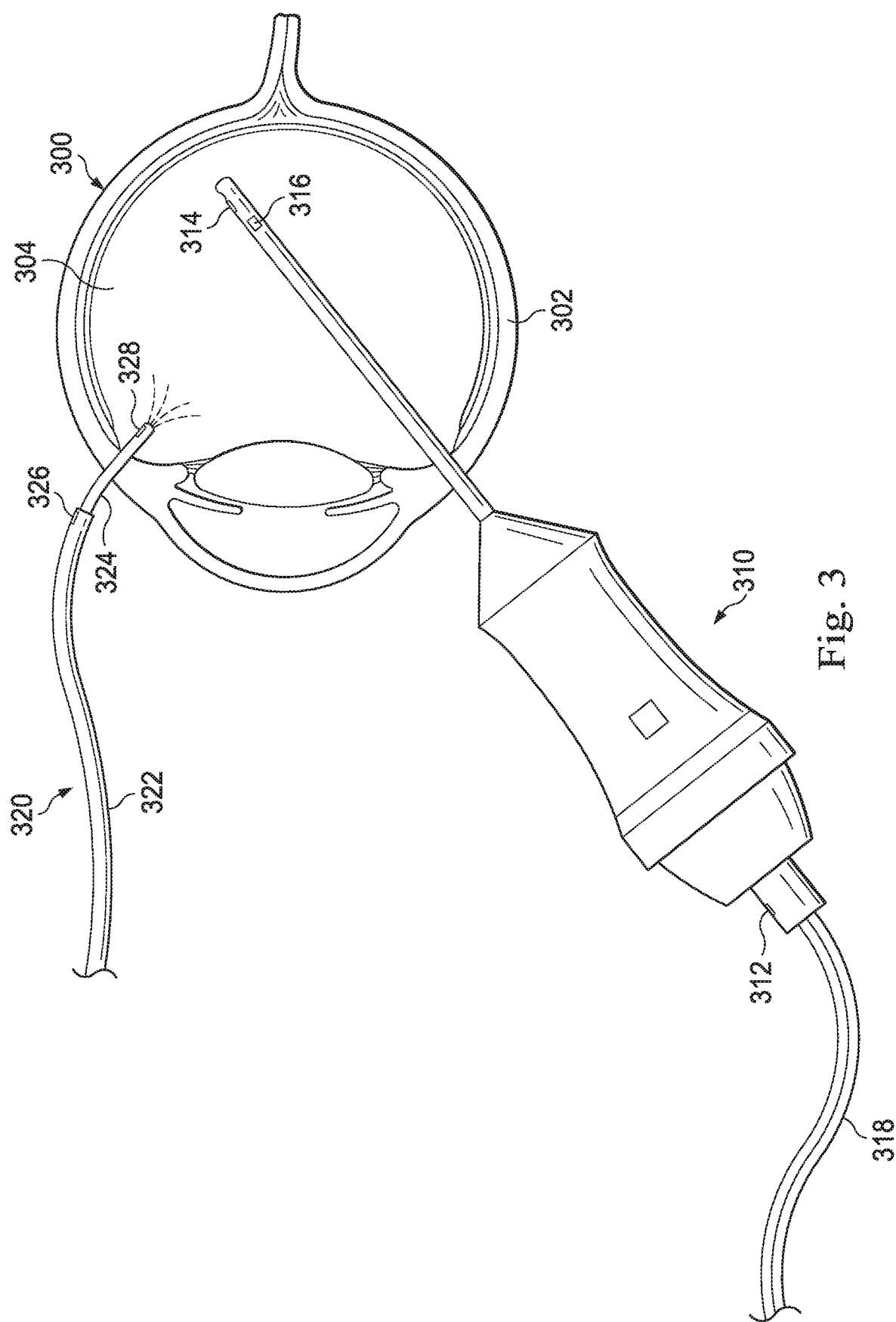
FIG. 3 is an illustration of a hand piece and an infusion line in situ in an eye according to exemplary aspects of the present disclosure.

FIG. 1 illustrates an ophthalmic surgical system 100 according to an exemplary embodiment. The surgical system 100 may include a console 102 that has a mobile base housing 103, an associated display screen 104 that may show data relating to system operations and performance during an ophthalmic surgical procedure, and a foot pedal 108 in communication with the console 102. The surgical system 100 also may include a hand piece 110 that may be utilized during an ophthalmic surgical procedure. Depending on the implementation, the hand piece 110 may be, for example, a vitrectomy cutter hand piece, an ultrasonic hand piece, an aspiration hand piece, a powered/active syringe or other hand piece. The surgical system 100 may also include an actuation line 112 having a proximal end coupled to the console 102 and a distal end coupled to the hand piece 110, and an infusion line 114 having a proximal end coupled to the console 102 and a distal end 120 having an infusion tip 121 configured to enter into a vitreous chamber of a patient's eye. The surgical system 100 may also include at least one IOP sensor 124, which may include, for example without limitation, a pressure sensor and/or a flow rate sensor. The IOP sensor 124 may be disposed adjacent to the distal end 120 of the infusion line 114 as shown in FIG. 1. Alternatively, or in addition, the IOP sensor 124 may be disposed at the distal end 120 of the infusion line 114 and/or at a distal end of the hand piece 110 and configured to enter into the vitreous chamber of the patient's eye, as shown in FIG. 3.

The console 102 of the surgical system 100 includes features that allow for control of the hand piece 110. For example, the actuation line 112 may include pneumatic and/or electrical supply lines to couple the hand piece 110 to the console 102. The actuation line 112 may facilitate control and monitoring of the hand piece 110 by transmitting data between the hand piece 110 and the console 102.

The console 102 of the surgical system 100 further includes features that allow communication of sensor data between the IOP sensor 124 and the console 102. For example, the infusion line 114 may include electrical supply lines to couple the IOP sensor 124 to the console 102. The infusion line 114 may facilitate taking measurements at the IOP sensor 124 by transmitting data between the IOP sensor 124 and the console 102.

The console 102 further includes a computer system (FIG. 2) that may include one or more processors in communication with a memory having computer instructions to control the hand piece 110, display information on the screen 104, and receive and process input commands and data. The surgical system 100 may include a network interface for communication with a network. These features facilitate control and monitoring of the hand piece 110 during operation. Additionally, these features may facilitate the monitoring, data processing, and control for the IOP sensor 124. Some embodiments of the surgical system 100 further include a pressure sensor 106 disposed on or about the mobile base housing 103 to sense an ambient pressure. This ambient pressure may be atmospheric pressure.

Some aspects of the surgical system 100, such as the hand piece 110, the infusion line 114, and the IOP sensor 124, are described in further detail in U.S. patent application Ser. No. 14/090,360, filed on Nov. 26, 2013, entitled "Pressure-Sensing Vitrectomy Surgical Systems and Methods," which is hereby incorporated by reference in its entirety.

Figure 2:
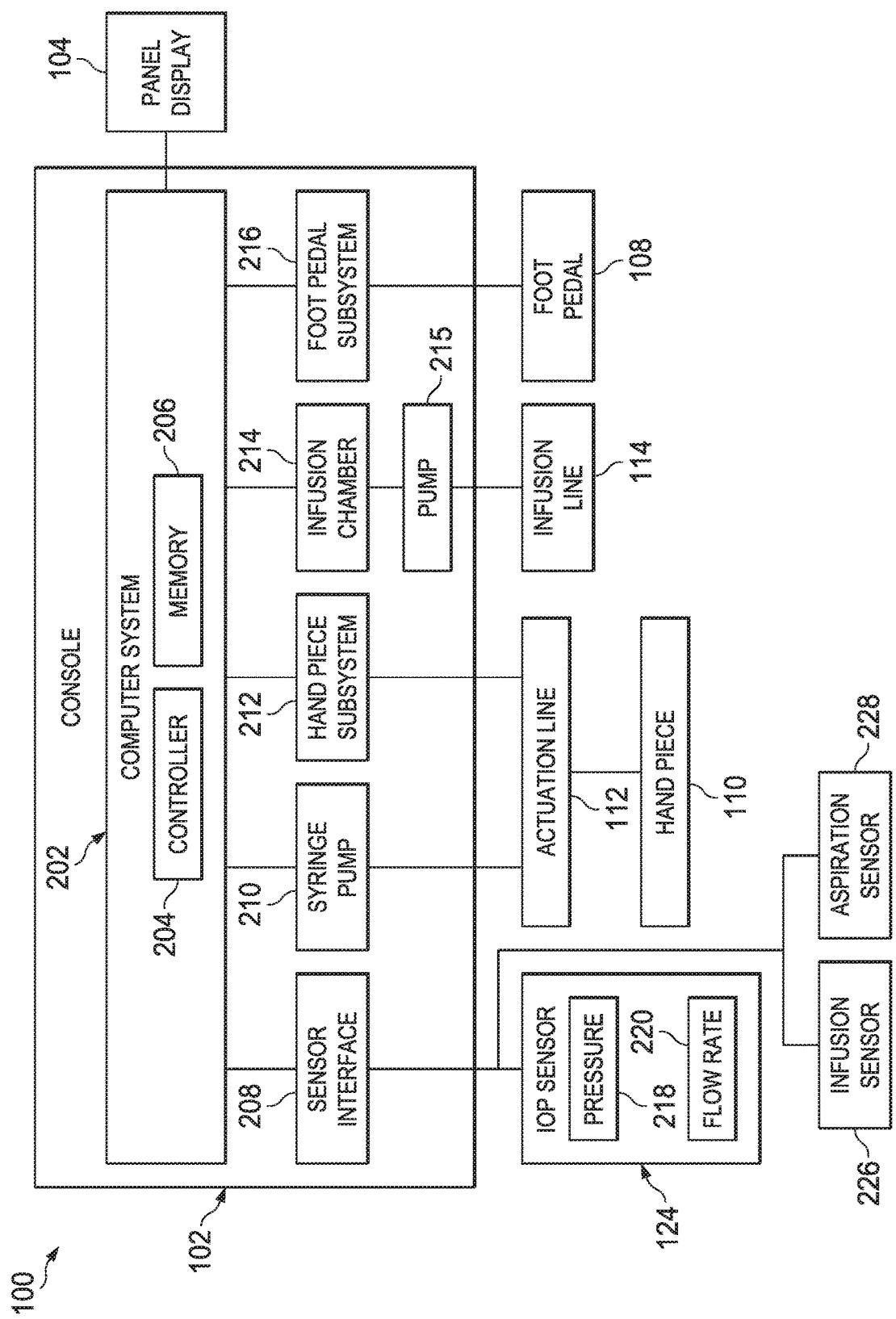
FIG. 2 is a block diagram of the surgical system of FIG. 1 showing various subsystems according to exemplary aspects of the present disclosure.

FIG. 2 is a block diagram of the surgical system 100 of FIG. 1 showing various subsystems. The console 102 includes a computer system 202, which includes a controller 204 and a memory 206. The console 102 further includes a sensor interface 208, a syringe pump 210, a hand piece subsystem 212, an infusion chamber 214, an infusion drive mechanism such as an infusion pump 215, and a foot pedal subsystem 216. The infusion pump 215 may be a part of the infusion chamber 214 or may be provide as a separate component coupled to the infusion chamber 214.

The controller 204 may be one or more processors such as microprocessors, logic devices, microcontrollers, application specific integrated circuits (ASICs), programmable logic devices (PLDs), or other suitable processing systems and be configured to run operating systems and applications. The controller 204 is configured to execute computer instructions stored on the memory 206 and access data stored in memory 206. Further, the controller 204 is configured to display information on panel display screen 104.

The controller 204 is configured to receive, through the sensor interface 208, sensor data relating to an IOP of a patient's eye from the IOP sensor 124, an infusion sensor 226, and/or an aspiration sensor 228. The IOP sensor 124 may be disposed adjacent to the patient's eye during the ophthalmic surgical procedure. The IOP sensor 124 may be configured to determine, at a location adjacent to the patient's eye, the sensor data, and provide the sensor data to the controller 204. For example, in some implementations, the IOP sensor 124 may be disposed adjacent to the distal end 120 of the infusion line 114 such that the IOP sensor 124 is just outside the eye and just upstream of the infusion line 114 during the ophthalmic surgical procedure. The IOP sensor 124 may include a pressure sensor 218 (e.g., fiber optic pressure sensors, electrical pressure sensors such as piezoelectric pressure sensors, microelectromechanical system (MEMS) pressure sensors, or other pressure sensors) that measures a pressure (e.g., a pressure drop just outside the eye, which may not be able to be accurately measured by a pressure sensor located inside the console 102) and/or a flow rate sensor 220 that measures a flow rate of fluid through a tubing such as the infusion line 114. The controller 204 may calculate an IOP value, such as a predicted IOP value, based on the sensor data, which may include one or both of the pressure data and the flow rate data.

Alternatively, or in addition, the IOP sensor 124 may be disposed inside the patient's eye during the ophthalmic surgical procedure. The IOP sensor 124 may be configured to determine, at a location in the vitreous chamber, the sensor data and provide the sensor data to the controller 204. For example, the IOP sensor 124 may be disposed at the distal end 120 of the infusion line 114 such that the IOP sensor 124 is in the vitreous chamber of the patient's eye during the ophthalmic surgical procedure. The IOP sensor 124 may include the pressure sensor 218 that measures pressure data. The controller 204 may calculate an IOP value, which may be an actual IOP value when the IOP sensor 124 is located in the patient's eye, based on the sensor data, which includes the pressure data.

Implementations including the infusion sensor 226 or the aspiration sensor 228 monitor or detect the flow rate of fluid entering the patient's eye or leaving the patient's eye. For example, the infusion sensor 226 may be associated with the infusion line 114 in a manner permitting it to monitor or detect pressure in the infusion line, flow through the infusion line, or some other parameter indicative of pressure or flow. In some implementations, the infusion sensor 226 monitors a pump speed of the infusion pump 215. In some such implementations, the infusion sensor is simply feedback from a processor or motor on the infusion pump 215 indicative of the pump speed. In some implementations, the infusion sensor 226 may include a pressure sensor or flow rate sensor as described above with reference to the IOP sensor.

The actuation line 112 may be used to inject viscous fluid (e.g., liquid tamponades) into or remove viscous fluid from the vitreous chamber. The syringe pump 210 may supply pressures into the actuation line 112. The actuation line 112 has the proximal end coupled to the console 102, the distal end coupled to the hand piece 110. In some implementations, the hand piece 110 may include a powered syringe configured to inject or extract viscous fluid into or from the eye. The syringe pump 210 may provide a positive pressure or a negative pressure that injects or extracts the viscous fluid in the powered syringe into or away from the eye. The syringe pump 210 is connected with the actuation line 112 and the hand piece 110. The syringe pump 210 may provide positive or negative pressure for viscous fluid injection and/or extraction from the vitreous chamber by the hand piece 110.

The hand piece 110 may be in communication with the hand piece subsystem 212 via a pneumatic or electrical line provided in the actuation line 112. The controller 204, which is in communication with the hand piece subsystem 212, may control one or more aspects of the hand piece 110, such as an on or off state or a cutting rate of the hand piece 110.

The infusion line 114 is used to deliver low viscosity fluid (e.g., a liquid such as balanced salt solution (BSS®), a gas such as air, or other fluid) such as replacement fluid or irrigation fluid from the infusion chamber 214 into the vitreous chamber. The infusion chamber 214 is in fluid communication with the infusion line 114. The infusion line 114 may have the proximal end coupled to the console 102, the distal end (e.g., an engagement member) 120 configured to enter into the vitreous chamber of the patient's eye, and an infusion passage extending therethrough. The infusion chamber 214 may be in fluid communication with the infusion passage through the infusion line 114, and the infusion passage is in fluid communication with the vitreous chamber of the patient's eye.

The infusion chamber 214 may store low viscosity fluid and is configured to provide fluid infusion into the vitreous chamber through the infusion passage of the infusion line 114. Some implementations employ the infusion pump 215 to infuse fluid to or otherwise irrigate the surgical site. The infusion pump 215 may be any of a variety types of pumps, including a peristaltic pump, a syringe pump, a pressurized fluid pump, or some other infusion pump. Control of the pump may permit the computer system 202 to increase, decrease, or hold steady flow through the pump based on received information from the infusion sensor 226, the foot pedal subsystem, or other information. In some implementations, the computer system 202 may include a pre-stored threshold that serves as an upper limit for fluid flow rate or pressure introduced to the surgical site through the infusion line. In such implementations, if the requested fluid amount exceeds the threshold, the infusion pump 215 may be disabled or its speed may be capped to avoid damage to the sensitive tissues in the patient's eye.

The foot pedal 108 receives actuation from a foot of a user and transmits actuation data to the foot pedal subsystem 216. The foot pedal subsystem 216 includes an interface between the foot pedal 108 and the controller 204, and may receive actuation data from the foot pedal 108, process the actuation data, and transmit the actuation data to the controller 204. The controller 204 receives the actuation data from the foot pedal subsystem 216 and, in response, may regulate the syringe pump 210, fluid infusion through the infusion line 114, and/or one or more aspects of the hand piece 110 based on the actuation data, as further described herein. The foot pedal 108 may be a wired foot pedal as shown in FIG. 1 or a wireless foot pedal (not shown).

The controller 204 monitors for changes in the IOP based on the sensor data, and regulates the viscous fluid delivery and/or removal from the vitreous chamber of the patient's eye by the hand piece 110 based on the changes in the IOP. In some implementations, the controller 204 may control the syringe pump 210 to regulate the viscous fluid delivery/removal from the vitreous chamber. For example, the controller 204 may control the syringe pump 210 by reducing a pressure generated by the syringe pump 210 in response to the IOP (e.g., an IOP value such as a predicted IOP value or an actual IOP value) exceeding a threshold IOP level (e.g., a threshold value). In another example, the controller 204 may turn on a negative pressure generated by the syringe pump 210 in response to the IOP rising above a threshold and/or an actuation of the foot pedal 108. Accordingly, the controller 204 may perform automatic braking of the viscous fluid delivery/removal by the hand piece 110. In a further example, the controller 204 may control the syringe pump 210 based on a difference between the IOP and a target IOP level (e.g., a target value or range) to reduce the difference between the IOP and the target IOP level.

FIG. 3 illustrates a cross-sectional view of an eye 300 undergoing a procedure involving a hand piece 310 (e.g., the hand piece 110 in FIGS. 1 and 2) and an infusion line or infusion cannula 320 (e.g., the infusion line 114 in FIGS. 1 and 2). Both the hand piece 310 and the infusion line 320 may be coupled to a console (e.g., the console 102 in FIGS. 1 and 2). In FIG. 3, the hand piece 310 and the infusion line 320 are respectively inserted through the sclera 302 and into the vitreous chamber 304 of the eye 300. The infusion line 320 is used to deliver low viscosity fluid such as replacement fluid or irrigation fluid into the vitreous chamber 304 during an ophthalmic surgical procedure (e.g., vitrectomy, fluid/air exchange, air/gas exchange, silicone oil injection, and/or other ophthalmic surgical procedures). Fluid infusion may be regulated by increasing or decreasing a pressure level of the irrigation fluid by a surgical system (e.g., the surgical system 100 of FIGS. 1 and 2). The hand piece 310 may be a powered/active syringe (e.g., pneumatic, hydraulic, electric, etc.).

The infusion line 320 includes a flexible elongate member 322. Some implementations include a rigid engagement member 324 (e.g., the distal end in FIG. 1) affixed at the distal end. The rigid engagement member 324 may be more rigid than the flexible elongate member 322. The flexible elongate member 322 and the rigid engagement member 324 have a central lumen (e.g., an infusion passage) running therethrough. The infusion line 320 may provide low viscosity fluid to the vitreous chamber 304 from a fluid source (e.g., the infusion chamber 214 in FIGS. 1 and 2), carried through the central lumen, in order to maintain an appropriate IOP as portions of the vitreous humor and/or fluid in the vitreous chamber 304 are removed.

In some implementations, the infusion line 320 may include one or more pressure sensors, for example, a pressure sensor 326, a pressure sensor 328, or both. In some implementations, one or more of the pressure sensors 326 and 328 may correspond with the IOP sensor 124, and in some implementations, one or more of the pressure sensors 326 and 328 may correspond with the infusion sensor 226. The pressure sensor 326 may be disposed on the infusion line 320 and adjacent to the distal end of the infusion line 320 such that it remains outside, but in close proximity to, the eye 300 during the ophthalmic surgical procedure. In some implementations, the pressure sensor 328 may sense a pressure just outside the eye 300, which may be used to determine the IOP (e.g., an actual IOP value or a predicted IOP value that is closer to an actual IOP value than possible using sensors located in the console) during the surgical procedure. In some implementations, the pressure sensor 328 is disposed on the rigid engagement member 324 (e.g., at a distal portion of the rigid engagement member 324) such that it enters into the vitreous chamber 304 during the ophthalmic surgical procedure. The pressure sensor 328 may sense an internal eye pressure in the vitreous chamber 304, which may be used to determine the IOP (e.g., an actual IOP value) during the surgical procedure.

Depending on the implementation, the hand piece 310 may include one or more pressure sensors, such as a pressure sensor 312, a pressure sensor 314, and/or a pressure sensor 316. Each of the pressure sensors 312, 314, and 316 may measure a pressure at a different location. In some implementations, one or more of the pressure sensors 312, 314, and 316 may correspond with the IOP sensor 124, and in some implementations, one or more of the pressure sensors 326 and 328 may correspond with the aspiration sensor 228. Depending on the implementation, the pressure sensor 312 may be disposed on a housing of the hand piece 310 and may measure an ambient pressure such as atmospheric pressure. In some examples, the ambient pressure sensor 312 is provided as pressure sensor 106 on an exterior surface of the console 102, as shown in FIG. 1. The pressure sensors 314 and 316 may be disposed at a tip (e.g., a cutter) of the hand piece 310. The pressure sensor 314 may be disposed on the hand piece 310 and may measure an internal eye pressure in the vitreous chamber 304 outside the cutter, which may be used to determine the IOP (e.g., an actual IOP value) during the ophthalmic surgical procedure. The pressure sensor 316 may be disposed within the tip so as to measure an internal pressure that is internal to the hand piece, which may be used to characterize the pressure supplied through actuation line 318 (e.g., the actuation line 112 in FIGS. 1 and 2) to the hand piece 310.

In addition to their respectively sensed pressures, pressure sensors 312, 314, 316, 326, and/or 328 may be used in conjunction to provide a differential pressure, such as a pressure representative of the IOP of the eye 300. Generally, the IOP is a gauge pressure reading determined by the difference between the absolute pressure in the eye (as measured by a pressure sensor in the eye such as the pressure sensor 314 and/or 328) and atmospheric pressure (as measured by the pressure sensor 312 and/or pressure sensor 106 in FIG. 1). Therefore, in some exemplary embodiments, pressure readings of pressure sensor 314 and/or 328 are taken simultaneously or nearly simultaneously with pressure readings of atmospheric pressure sensor 312 and/or 106 so that the actual IOP can be calculated as a function of the measured pressures.

The pressure sensors 312, 314, 316, 326, and 328 may each be a fiber optic pressure sensor, an electrical pressure sensor such as a piezoelectric pressure sensor, a MEMS pressure sensor, or another pressure sensor. The pressure sensors 314, 316, and 328 may be miniaturized pressure sensors capable of entering a small orifice through which the cutter of the hand piece 310 or the engagement member 324 enters the eye 300. As the pressure sensors 312 and 326 are disposed outside the eye and do not enter the eye through the small orifice, the pressure sensors 312 and 326 do not have size constraints and, thus, are not limited to such miniaturized pressure sensors. Accordingly, the pressure sensors 312 and 326 may be any appropriate type of pressure sensor.

The pressures that may be sensed by the hand piece 310 and/or the infusion line 320 facilitate improved control by the surgical system by providing additional information that can be processed by the surgical system and used for automated flow and pressure control. For example, by measuring and determining the IOP of the eye 300, the surgical system may be able to avoid the collapse or pressure spike of the eye 300 due to excessive delivery or excessive removal of viscous fluid by the hand piece 310 during an ophthalmic surgical procedure by automatically adjusting the supplied injection/extraction pressure.

As illustrated in FIG. 3, some embodiments may include redundant pressure sensors. For example, the pressure sensor 328 of the infusion line of 320 may be considered redundant due to the presence of the pressure sensor 314 of the hand piece 310. In some embodiments, only one pressure sensor to measure an internal eye pressure may be provided by the combined use of the hand piece 310 and the infusion line 320, such that either the hand piece 310 or the infusion line 320 includes a pressure sensor within the vitreous chamber 304. Similarly, in some embodiments only one ambient pressure sensor is present. In other embodiments, data for a single pressure is obtained using multiple pressure sensors. The data from each pressure sensor may be provided directly or a mathematical combination of the pressure sensors may be used to provide a single value. Using the pressure measurements obtained from the pressure sensors depicted in FIG. 3, the surgical system may automatically control viscous fluid injection/extraction and, further, may allow a surgeon to exercise improved control of hand piece 310 and the infusion line 320 during a surgical procedure.

Figure 4:
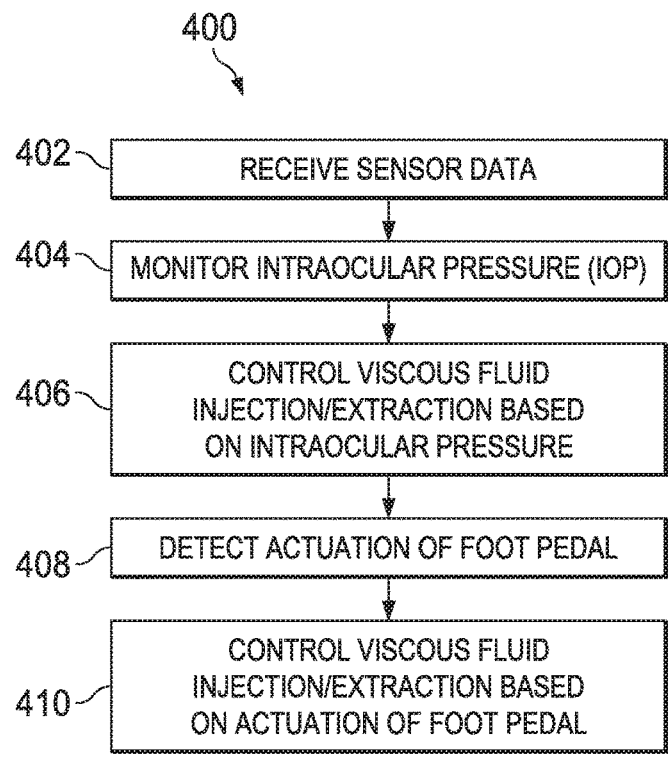
FIG. 4 is a flowchart showing a process performed by the surgical system of FIGS. 1 and 2 for automating viscous fluid injection/extraction responsive to changes in intraocular pressure (IOP) during an ophthalmic surgical procedure according to exemplary aspects of the present disclosure.

FIG. 4 is a flowchart showing a process 400 performed by the surgical system 100 of FIGS. 1 and 2 for automating viscous fluid delivery/removal in a patient's eye during an ophthalmic surgical procedure.

At block 402, a controller such as the controller 204 of the surgical system 100 receives sensor data from one or more sensors such as the IOP sensor 124 disposed adjacent to or in the patient's eye.

At block 404, the controller 204 monitors for changes in IOP. The controller 204 may determine an IOP (e.g., an IOP value such as a predicted IOP value or an actual IOP value) based on the sensor data and detect changes in the IOP.

At block 406, the controller 204 regulates viscous fluid delivery/removal responsive to the changes in the IOP. The controller 204 may control the syringe pump 210 to regulate the viscous fluid delivery/removal in response to the changes in the IOP. The syringe pump 210 may provide injection/extraction pressure to the hand piece 110 which performs viscous fluid injection or extraction from a vitreous chamber of the patient's eye.

For example, the controller 204 may provide threshold control of the syringe pump 210 such that in response to the IOP falling below a threshold such as a threshold IOP level (e.g., a threshold value), the controller 204 automatically reduces a negative pressure generated by the syringe pump 210 and/or automatically increases a positive pressure generated by the syringe pump 210. Further, the controller 204 may, in response to the IOP rising above the threshold, automatically increase the negative pressure generated by the syringe pump 210 and/or reduce the positive pressure generated by the syringe pump 210.

In another example, the controller 204 may provide on/off control of the syringe pump 210 such that in response to the IOP falling below or rising above a threshold, the controller 204 automatically turns on/off the syringe pump 210. In a further example, the controller 204 may provide control-loop feedback control such as proportional-integral-derivative (PID) control of the syringe pump 210. The controller 204 may determine a difference between the IOP and a target IOP level (e.g., a target value or range) and, in response, automatically adjust the syringe pump 210 to reduce the difference between the IOP and the target IOP level.

Advantageously, the surgical system 100 safeguards against low or high IOP and prevents collapsing or overfill of the eye.

In some implementations, the regulation of the viscous fluid injection/aspiration, by control of the syringe pump 210 or otherwise, may be coordinated with regulation of the low viscosity fluid infusion/aspiration. The controller 204 may prioritize regulating viscous fluid injection/extraction, prioritize regulating low viscosity fluid infusion/aspiration, or simultaneously regulate viscous and low viscosity fluid infusion/aspiration.

At block 408, the controller 204 may detect an actuation of the foot pedal 108. For example, the controller 204 may detect the actuation of the foot pedal 108 through a foot pedal subsystem such as the foot pedal subsystem 216. The controller 204 may receive actuation data from the foot pedal 108 through the foot pedal subsystem 216. The actuation data may indicate, for example, whether the foot pedal 108 is actuated, how far the foot pedal 108 is depressed, and/or how fast the foot pedal 108 is depressed.

At block 410, the controller 204 may control the viscous fluid injection or extraction based on the actuation of the foot pedal 108. For example, based on the actuation of the foot pedal 108 by the user, the controller 204 may control the syringe pump 210 to maintain, increase, or decrease the viscous fluid injection or extraction pressure.

Figure 5:
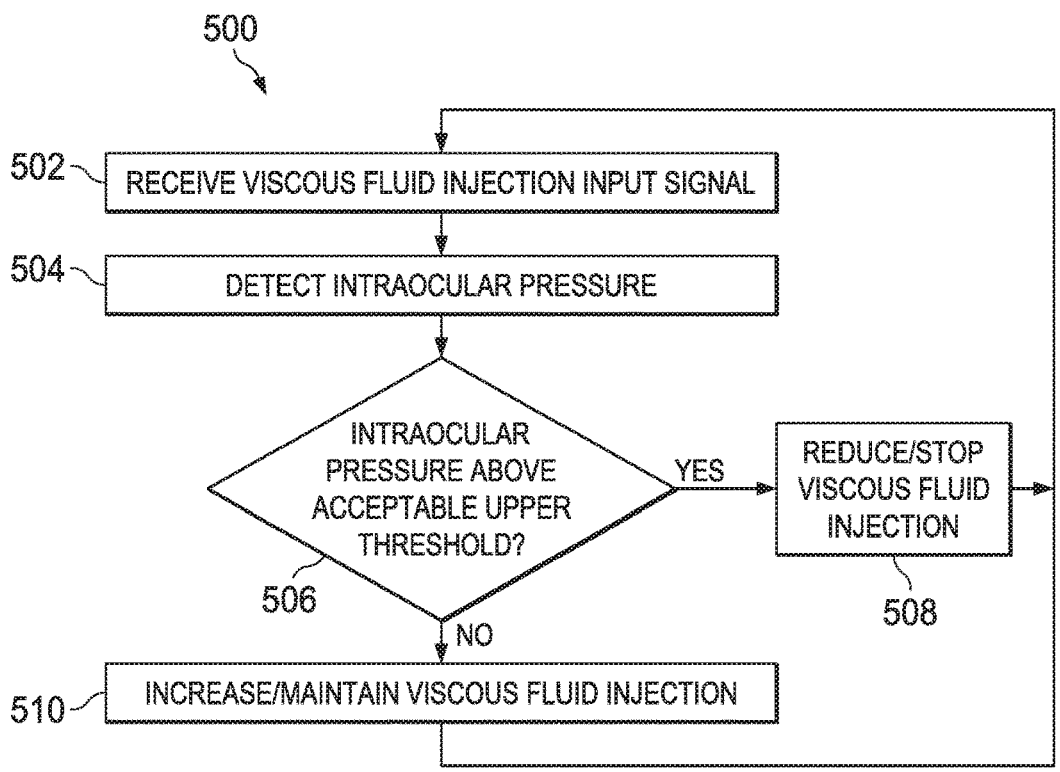
FIG. 5 is a flowchart showing a process performed by the surgical system of FIGS. 1 and 2 for injecting or delivering viscous fluid into an eye during an ophthalmic surgical procedure according to exemplary aspects of the present disclosure.
Figure 6:
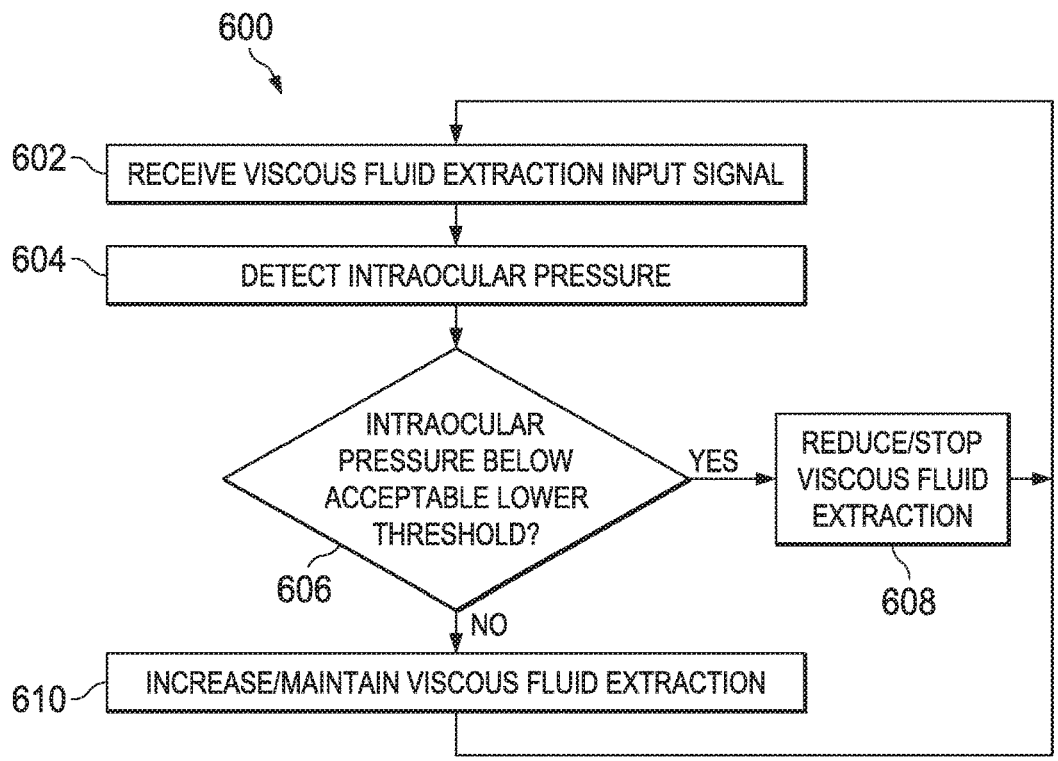
FIG. 6 is a flowchart showing a process performed by the surgical system of FIGS. 1 and 2 for extracting or removing viscous fluid from an eye during an ophthalmic surgical procedure responsive to changes in IOP according to exemplary aspects of the present disclosure.

FIG. 5 shows exemplary implementation of a viscous fluid injection/delivery control responsive to changes in IOP. FIG. 6 shows exemplary implementation of a viscous fluid extraction/removal control responsive to changes in IOP. Accordingly, FIGS. 5 and 6 each show different implementations that may make up a part of blocks 406-410 in FIG. 4.

As shown in FIG. 5, during a viscous fluid injection/delivery process, the controller 204 may regulate the injection/delivery of viscous fluid in response to changes in IOP. During a vitreoretinal surgical procedure, after the vitreous is cut and removed (e.g., aspirated), the eye may be filled with a salt solution (e.g., BSS) and repair procedures may be performed (e.g., repair retinal). After the repair procedure is completed, the salt solution in the eye may be replaced with air. A viscous fluid, such as a liquid tamponade (e.g., silicone oil or perfluoron solution), may then be injected into the eye by a hand piece 110 to replace the air. The liquid tamponade may fill the eye to seal retinal tears and allow for scar formation. During the viscous fluid injection process, the air or air pressure may be delivered via infusion line 114 or 320. In some embodiments, the air pressure from infusion line 114 or 320 may be maintained at a constant level as the viscous fluid is introduced to replace the air and to fill the eye.

At block 502, the controller 204 may receive a control signal to inject/deliver the viscous fluid into the eye. The control signal may be input by the user/surgeon at the foot pedal 108. For example, the user/surgeon may press on the foot pedal 108 to generate an injection signal to the controller 204 instructing the controller 204 to inject or pump viscous fluid into the eye via the hand piece 110 or 310.

At block 504, the controller 204 may detect the IOP in the eye. As noted above, the IOP may be detected or estimated based on sensor signals received from one or more sensors. In some examples, the IOP or changes in IOP may be measured or calculated based on signal data output from the sensors.

At block 506, the controller 204 may determine whether the IOP is above an acceptable upper threshold. The acceptable upper threshold may be set automatically by the controller to a default value based on the safety recommendations for IOP. In some embodiments, the user/surgeon may input an upper limit for the IOP to avoid over-pressurizing the eye. The controller 204 the compare the detected or calculated IOP against the upper threshold value to determine whether the IOP has exceeded the upper threshold value. If so, the controller 204 may automatically reduce or stop the viscous fluid injection flow at block 508. For example, the controller 204 may stop or lower the injection pressure of the viscous fluid at the hand piece 110, such as by stopping the syringe pump 210. In another example, the controller 204 may open a pressure release valve (not shown) to relieve injection pressure. As such, even if the user/surgeon continues to press on the foot pedal 108 requesting more viscous fluid injection, the controller 204 may stop or reduce the viscous fluid flow/pressure to avoid over filling or over-pressurizing the eye. Accordingly, the controller 204 may override the user input to increase injection pressure when the IOP has already exceeded the safety limit.

If the controller 204 determines that the IOP does not exceed the upper threshold value, the controller 204 may increase or maintain the viscous fluid injection based on the viscous fluid injection signal input from the user/surgeon (e.g., via the foot pedal 108) at block 510. For example, the controller 204 detects an actuation of a foot pedal such as the foot pedal 108 by a user. The controller 204 may detect the actuation of the foot pedal 108 through a foot pedal subsystem such as the foot pedal subsystem 216. The controller 204 may receive actuation data from the foot pedal 108 through the foot pedal subsystem 216. The actuation data may indicate, for example, whether the foot pedal 108 is actuated, how far the foot pedal 108 is depressed, and/or how fast the foot pedal 108 is depressed.

If the controller 204 determines that the IOP does not exceed the upper threshold value, the controller 204 regulates the viscous fluid injection/delivery responsive to actuation of the foot pedal 108. The controller 204 may further control the syringe pump to regulate the viscous fluid injection into the vitreous chamber of the patient's eye. For example, if the controller 204 provides on/off control, the controller 204 may, in response to the actuation of the foot pedal 108, turn on the syringe pump 210. In another example, if the controller 204 provides control-loop feedback control, the controller 204 may, in response to the actuation of the foot pedal 108, adjust the syringe pump 210 such as by adjusting the positive pressure generated by the syringe pump. Thus, the controller 204 may control the syringe pump to maintain or increase the positive pressure to maintain or increase the viscous fluid injection into the eye. Accordingly, the controller 204 may continuously monitor the IOP and may automatically control the viscous fluid injection based on IOP to avoid overfilling or over-pressurizing the eye during a viscous fluid injection/delivery process.

Referring now to FIG. 6, during a viscous fluid extraction/removal process, the controller 204 may regulate the extraction/removal of viscous fluid in response to changes in IOP. After the retinal tears are sealed and scar has formed, the patient may returned for a follow up procedure to remove the viscous fluid (liquid tamponade) from the eye. Typically, in the follow up procedure, the viscous fluid (liquid tamponade) may be removed and replaced with a low viscosity fluid, such as a salt solution. The viscous fluid may be extracted by the hand piece 110 while the salt solution is infused into the eye by the infusion line 114.

At block 602, the controller 204 may receive a control signal to remove the viscous fluid from the eye. The control signal may be input by the user/surgeon at the foot pedal 108. For example, the user/surgeon may press on the foot pedal 108 to generate an extraction signal to the controller 204 instructing the controller 204 to remove or suction the viscous fluid from the eye via the hand piece 110 or 310.

At block 604, the controller 204 may detect the IOP in the eye. As noted above, the IOP may be detected or estimated based on sensor signals received from one or more sensors. In some examples, the IOP or changes in IOP may be measured or calculated based on signal data output from the sensors.

At block 606, the controller 204 may determine whether the IOP is below an acceptable lower threshold. The acceptable lower threshold may be set automatically by the controller 204 as a default value based on the general safety recommendations for IOP. In some embodiments, the user/surgeon may input a lower limit for the IOP to avoid under-pressurizing or collapsing the eye. The controller 204 may compare the detected or calculated IOP against the lower threshold value to determine whether the IOP has dropped below the lower threshold value. If so, the controller 204 may automatically reduce or stop the viscous fluid removal/extraction flow at block 608. For example, the controller 204 may stop or lower the negative pressure generated by the syringe pump 210 to reduce the extraction flow of the viscous fluid at the hand piece 110. As such, even if the user/surgeon continues to press on the foot pedal 108 requesting more viscous fluid removal, the controller 204 may stop or reduce the viscous fluid extraction pressure to avoid collapsing or under-pressurizing the eye. Accordingly, the controller 204 may override the user input to increase vacuum pressure when the IOP has already dropped under than the safety limit.

If the controller 204 determines that the IOP does not drop below the lower threshold value, the controller 204 may increase or maintain the viscous fluid extraction/removal based on the viscous fluid extraction signal input from the user/surgeon (e.g., via the foot pedal 108) at block 610. For example, the controller 204 detects an actuation of a foot pedal such as the foot pedal 108 by a user. The controller 204 may detect the actuation of the foot pedal 108 through a foot pedal subsystem such as the foot pedal subsystem 216. The controller 204 may receive actuation data from the foot pedal 108 through the foot pedal subsystem 216. The actuation data may indicate, for example, whether the foot pedal 108 is actuated, how far the foot pedal 108 is depressed, and/or how fast the foot pedal 108 is depressed.

If the controller 204 determines that the IOP does not drop below the lower threshold value, the controller 204 regulates the viscous fluid extraction/removal responsive to actuation of the foot pedal 108. The controller 204 may further control the syringe pump 210 to regulate the viscous fluid extraction/removal from the vitreous chamber of the patient's eye. For example, if the controller 204 provides on/off control, the controller 204 may, in response to the actuation of the foot pedal 108, turn on the syringe pump 210. In another example, if the controller 204 provides control-loop feedback control, the controller 204 may, in response to the actuation of the foot pedal 108, adjust the syringe pump 210 such as by adjusting the negative pressure generated by the syringe pump 210. Thus, the controller 204 may control the syringe pump 210 to maintain or increase the negative pressure to maintain or increase the viscous fluid extraction/removal from the eye. Accordingly, the controller 204 may continuously monitor the IOP and may automatically control the viscous fluid extraction based on IOP to avoid collapsing or under-pressurizing the eye during a viscous fluid extraction/removal process.

In a further example, the controller 204 simultaneously regulates the removal of the viscous fluid and the infusion of the salt solution. In response to the IOP being below a threshold IOP level, the controller 204 simultaneously regulates infusion and extraction by adjusting both the infusion (e.g., by controlling pressure at the infusion line 114) and the extraction (e.g., by controlling the negative pressure at the actuation line 112) in a coordinated fashion. Alternatively, the regulation of viscous fluid extraction and the regulation of low viscosity fluid infusion are separately controlled, each having its own parameters, thresholds, and/or control operations or mechanisms.

Figure 7:
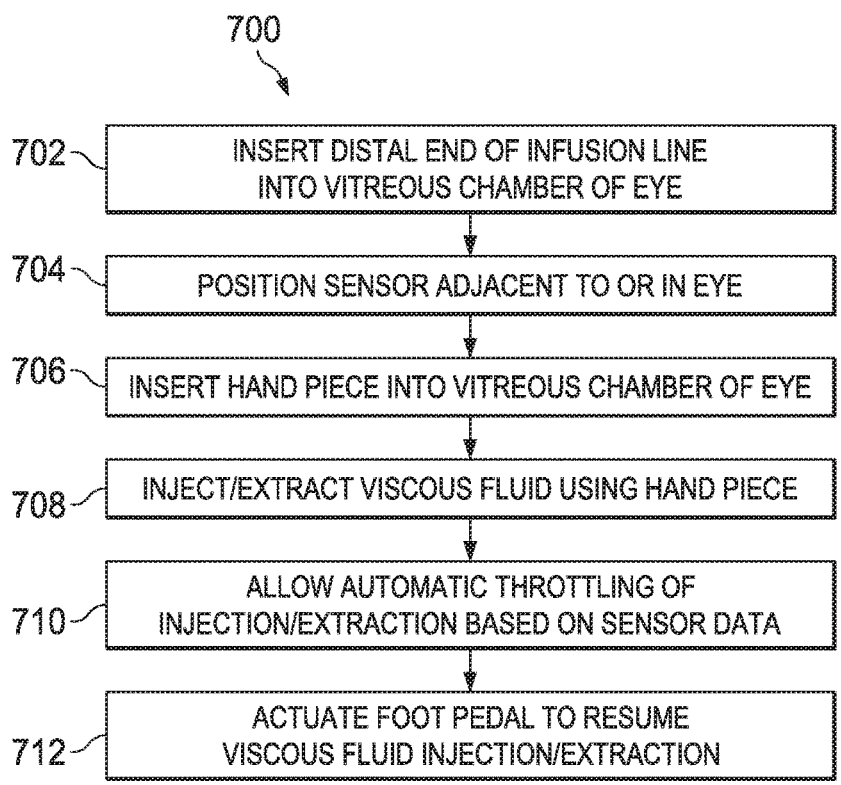
FIG. 7 is a flowchart showing a process for operating the surgical system of FIGS. 1 and 2 during an ophthalmic surgical procedure according to exemplary aspects of the present disclosure.

FIG. 7 is a flowchart showing a process 700 for operating the surgical system 100 of FIG. 1 during an ophthalmic surgical procedure.

At block 702, a user, such as a surgeon performing the ophthalmic surgical procedure, may insert a distal end of an infusion line such as the distal end (e.g., the engagement member) 120 of the infusion line 114 into a vitreous chamber of the patient's eye.

At block 704, the user may position a sensor such as the IOP sensor 124 adjacent to (e.g., in close proximity to) or inside a patient's eye. In embodiments in which the IOP sensor 124 is disposed adjacent to and/or at the distal end 120 of the infusion line 114 (e.g., sensor 326 and/or 328 in FIG. 3), block 706 is accomplished by performing block 702. In embodiments in which the IOP sensor 124 is disposed on the tip of the hand piece 110 (e.g., sensor 314 in FIG. 3), block 706 is accomplished by performing block 704. In other embodiments, the IOP sensor 124 is coupled to a separate line from the actuation line 112 and the infusion line 114, and the user places the IOP sensor 124 adjacent to and/or in the patient's eye separately from the actuation line 112 and the infusion line 114.

At block 706, the user inserts a tip of a hand piece such as the hand piece 110 into the vitreous chamber of the patient's eye. The hand piece 110 is coupled to a distal end of the actuation line 112.

At block 708, the user may inject or extract viscous fluid from the vitreous chamber of the patient's eye using the hand piece 110, which is powered by the syringe pump 210 in the console 102.

At block 710, the user allows automatic throttling of the viscous fluid based on sensor data measured by the IOP sensor 124. The surgical system 100 (e.g., by the controller 204) automatically regulates the viscous fluid injection/extraction based on the sensor data measured by the IOP sensor 124, as further described above in connection with controller 204 of FIG. 2 and block 406 of FIG. 4. For example, the surgical system 100 may automatically turn off or reduce a negative pressure generated by the syringe pump 210 in response to the IOP being lower than (or equal to or lower than) a threshold IOP level (e.g., a threshold value). In another example, the surgical system 100 may automatically turn off or reduce a positive pressure generated by the syringe pump 210 in response to the IOP being larger than (or equal to or larger than) a threshold IOP level (e.g., a threshold value).

At block 712, the user actuates a foot pedal such as the foot pedal 108 to control the viscous fluid injection/extraction. For example, the user may actuate the foot pedal 108 to resume viscous fluid extraction from the vitreous chamber of the patient's eye or increase the negative pressure generated by the syringe pump 210. In another example, the user may actuate the foot pedal 108 to resume viscous fluid injection into the vitreous chamber of the patient's eye or increase the positive pressure generated by the syringe pump 210.

In some embodiments, other types of powered syringes besides pneumatic powered syringes may be used. For example, hydraulic powered or electric powered syringes may be used for viscous fluid injection/extraction. The controller 204 may similarly control the injection/extraction of viscous fluid by these other types of powered/active syringes. Besides liquid tamponades, the system may also automatically regulate the injection/extraction of other types of viscous fluids for eye surgical procedures, such as stem cells, adhesives, and the like.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical system, comprising:
   a first pump connected with a first actuation line, the first pump being configured to provide an injection pressure for viscous fluid injection in a vitreous chamber of an eye of a patient;
   a second pump connected with a second actuation line, the second pump being configured to provide an extraction pressure for low viscosity fluid extraction in the vitreous chamber of the eye of the patient;
   a controller;
   a sensor disposed adjacent to a distal end of the second actuation line, the sensor configured to:
     detect the intraocular pressure (IOP) of the eye;
     generate sensor data based on the detected IOP; and
     provide the sensor data to the controller;
   a foot pedal system configured to receive user input for controlling injection of the viscous fluid in the eye; and
   wherein the controller is configured to:
     set an upper pressure threshold value;

receive the sensor data relating to the IOP of the eye;
receive the user input from the foot pedal system indicating a user request for more viscous fluid injection;
compare the IOP to the upper pressure threshold value;
determine that the IOP exceeds the upper pressure threshold value;
override the user request and not increase viscous fluid injection;
control the first pump to reduce or stop the injection pressure; and
simultaneously, with controlling the first pump to reduce or stop the injection pressure, control the second pump to regulate the IOP in the eye.

2. The system of claim 1, wherein the viscous fluid comprises one or more of a silicone oil, a perfluoron solution, a stem cell solution, and an adhesive.

3. The system of claim 1, wherein the sensor data relating to IOP further comprises flow rate data.

4. The system of claim 1, wherein the low viscosity fluid is a gas.

5. The system of claim 1, wherein controlling the second pump comprises using a proportional-integral-derivative (PID) control for the second pump.

6. An ophthalmic surgical system, comprising:
an infusion line having a proximal end, a distal end, and an infusion passage extending therethrough, the distal end of the infusion line being configured to enter into a vitreous chamber of an eye of a patient;
an actuation line having a proximal end and a distal end;
a sensor disposed adjacent to the distal end of the infusion line, the sensor being configured to:
detect a pressure at a location adjacent to the eye of the patient;
generate sensor data based on the detected pressure; and
provide the sensor data to the controller; and
a console coupled to the proximal end of the infusion line and the proximal end of the actuation line, the console comprising:
a syringe pump configured to provide pressures for viscous fluid extraction in the vitreous chamber through the actuation line;
an infusion chamber in fluid communication with the infusion passage;
an infusion pump configured to provide low viscosity fluid infusion from the infusion chamber to the vitreous chamber through the infusion passage;
a foot pedal system configured to receive user input for controlling an extraction of the viscous fluid in the eye; and
a controller configured to:
set a lower pressure threshold value;
receive the sensor data relating to an intraocular pressure (IOP) of the eye, the sensor data being determined at the location adjacent to the eye;
receive the user input from the foot pedal system indicating a user request for more viscous fluid extraction;
compare the IOP to the lower pressure threshold value;
determine that the IOP is below the lower pressure threshold value;
override the user request and not increase viscous fluid extraction;
control the syringe pump to reduce or stop the extraction pressure; and
simultaneously, with controlling the syringe pump to reduce or stop the extraction pressure, control the infusion pump to regulate the IOP in the eye.

7. The system of claim 6, wherein the viscous fluid comprises one or more of a silicone oil, a perfluoron solution, a stem cell solution, and an adhesive.

8. The system of claim 6, wherein the sensor data relating to IOP further comprises flow rate data.

9. The system of claim 6, wherein the low viscosity fluid is a gas.

10. The system of claim 6, wherein controlling the infusion pump comprises using a proportional-integral-derivative (PID) control for the infusion pump.

11. A method, comprising:
providing an injection pressure, through a first pump, for viscous fluid injection in a vitreous chamber of an eye of a patient;
providing an extraction pressure, through a second pump, for low viscosity fluid extraction in the vitreous chamber of the eye of the patient;
receiving sensor data from a sensor adjacent to or in the eye of the patient, wherein the sensor is configured to:
detect a pressure in the vitreous chamber of the patient;
generate sensor data based on the detected pressure; and
provide the sensor data to a controller;
monitoring an intraocular pressure (IOP) of the eye based on the sensor data;
receiving user input indicating a user request for more viscous fluid injection or a user request for more viscous fluid extraction;
comparing the IOP to an upper pressure threshold value;
determining that the user input indicates a user request for more viscous fluid injection and the IOP exceeds the upper pressure threshold value;
overriding the user request and not increase viscous fluid injection; and
controlling the first pump to reduce or stop injection pressure of the viscous fluid injection and simultaneously, with controlling the first pump to reduce or stop injection pressure of the viscous fluid injection, controlling the second pump to regulate the IOP in the eye.

12. The method of claim 11, further comprising calculating the IOP based on sensor data, the sensor data including data related to pressure, flow rate, or both.

13. The method of claim 11 wherein the low viscosity fluid is a gas.

14. The method of claim 11, wherein controlling the second pump comprises using a proportional-integral-derivative (PID) control for the second pump.

* * * * *